(12) United States Patent
Jaeschke et al.

(10) Patent No.: US 9,221,802 B2
(45) Date of Patent: Dec. 29, 2015

(54) ARYLETHYNYL DERIVATIVES

(71) Applicant: Hoffmann-La Roche Inc., Little Falls, NJ (US)

(72) Inventors: Georg Jaeschke, Basel (CH); Lothar Lindemann, Basel (CH); Heinz Stadler, Basel (CH); Eric Vieira, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/669,653

(22) Filed: Mar. 26, 2015

(65) Prior Publication Data

US 2015/0197510 A1 Jul. 16, 2015

Related U.S. Application Data

(63) Continuation of application No. PCT/EP2013/069674, filed on Sep. 23, 2013.

(30) Foreign Application Priority Data

Sep. 27, 2012 (EP) ..................................... 12186265

(51) Int. Cl.
C07D 413/04 (2006.01)

(52) U.S. Cl.
CPC .................................... *C07D 413/04* (2013.01)

(58) Field of Classification Search
CPC ....................................................... C07D 413/04
USPC .......................................... 544/92; 514/230.5
See application file for complete search history.

(56) References Cited

U.S. PATENT DOCUMENTS 8,034,806 B2 * 10/2011 Conn et al. ............... 514/212.08

* cited by examiner

*Primary Examiner* — Kahsay Habte
(74) *Attorney, Agent, or Firm* — Tamara A. Kale

(57) ABSTRACT

The present invention relates to ethynyl derivatives of formula I

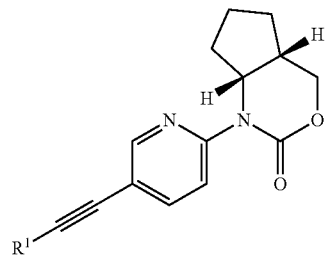

wherein
R[1] is phenyl, 3-fluorophenyl, 4-fluorophenyl or 2,5-di-fluorophenyl;
or to a pharmaceutically acceptable acid addition salt, in enantiomerically pure form with the absolute configuration as shown in formula I.
It has now surprisingly been found that the compounds of general formula I are allosteric modulators of the metabotropic glutamate receptor subtype 5 (mGluR5) which show advantageous biochemical-, physicochemical- and pharmacodynamic-properties compared to compounds of prior art.

5 Claims, No Drawings

ARYLETHYNYL DERIVATIVES

This is a continuation application of International Application No. PCT/EP2013/069674, filed Sep. 23, 2013, which claims the benefit of European Application No. 12186265.0, filed Sep. 27, 2012, each of which is incorporated herein by reference in its entirety.

The present invention relates to ethynyl derivatives of formula I

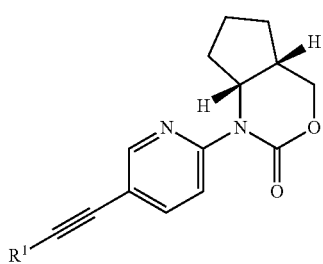

wherein
$R^1$ is phenyl, 3-fluorophenyl, 4-fluorophenyl or 2,5-di-fluorophenyl;
or to a pharmaceutically acceptable acid addition salt, in enantiomerically pure form with the absolute configuration as shown in formula I.

It has now surprisingly been found that the compounds of general formula I are allosteric modulators of the metabotropic glutamate receptor subtype 5 (mGluR5) which show advantageous biochemical-, physicochemical- and pharmacodynamic-properties compared to compounds of prior art.

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:
mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), tuberous sclerosis (TSC), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to a site different from the highly conserved orthosteric binding site. Allosteric modulators of mGluR5 have emerged recently as novel pharmaceutical entities offering this attractive alternative. Allosteric modulators have been described, for example in WO2008/151184, WO2006/048771, WO2006/129199, WO2005/044797 and in particular WO2011/128279 as well as in *Molecular Pharmacology*, 40, 333-336, 1991; *The Journal of Pharmacology and Experimental Therapeutics*, Vol 313, No. 1, 199-206, 2005; *Nature*, 480 (7375), 63-68, 2012;

Described in the prior art are positive allosteric modulators. They are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Allosteric modulation is thus an attractive mechanism for enhancing appropriate physiological receptor activation. There is a scarcity of selective allosteric modulators for the mGluR5 receptor. Conventional mGluR5 receptor modulators typically lack drug safety, which lead to more side effects of the drug.

Therefore, there remains a need for compounds that overcome these deficiencies and that effectively provide selective allosteric modulators for the mGluR5 receptor. The present invention solved this problem, as seen below:

Comparison of Compounds of the Invention Versus Similar Compounds of Prior Art:

Structurally similar compounds of prior art have been disclosed in WO2011128279 (=Ref. 1, Hoffmann-La Roche) and the structurally most similar compounds of this patent (examples 20, 72, 76, 79, 81 and 103) are shown for comparison.

Biological and Physicochemical Assays and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 μM) with on-line recording of fluorescence; in order to account for day-to-day variations in the responsiveness of cells, the $EC_{20}$ of glutamate was determined immediately ahead of each experiment by recording of a full dose-response curve of glutamate. Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response (=Efficacy) in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds which all have $EC_{50}$<30 nM.

Glutathione (GSH) Addition Assay after Metabolic Activation

The assay conditions for the detection of glutathione conjugates follow the procedure described by C. M. Dieckhaus et al. in Chem. Res. Toxicol., 18, 630-638 (2005). Samples for which the mass of a covalent adduct to a reactive metabolite was clearly detected are indicated as FLAG (positive). Compounds for which no adduct was detected are designated NO FLAG (negative).
Comparison of Compounds of the Invention Vs. Reference Compounds Ex. 20, 72, 76, 79, 81 and 103 of WO2011128279:

The compounds of the invention all have similar potencies compared to the reference compounds. Additionally they all show efficacies well below 60% compared to much higher values of the reference compounds (above 80%) which is a criteria with respect to tolerability issues of mGluR5 positive allosteric modulators. Compounds with high efficacy values above 60% show severe CNS related side-effects after oral dosing (seizures) at doses close to those where the desired therapeutic effects are observed (low therapeutic window). Compounds with efficacies below 60% are well tolerated at doses which may be 30 to 1000 times higher than the therapeutic dose while maintaining their desired therapeutic effects. Generally speaking, compounds of the present invention therefore have a clear advantage with respect to drug safety due to their efficacy values below 60% which correlates with the absence of severe CNS side-effect liabilities compared to structurally similar compounds of prior art. Surprisingly, some of the compounds of the invention also show a much better solubility compared to the reference compounds. It is well known to persons skilled in the art that better solubility leads to improved drug absorption as well as higher free fraction values which in turn lead to an increased availability of drug to its target. This is especially valid for drugs targeting the central nervous system compartment.

Finally the compounds of the invention do not show reaction with glutatione after metabolic activation (GSH assay). The reaction of chemically reactive drugs with proteins (covalent protein binding (CVB)) is an undesirable property with respect to drug safety. Proteins can form covalent adducts to reactive metabolites of drug molecules via their nucleophilic amino-acid side chains (e.g., cysteine, serine, lysine, etc.). Formation of drug-protein adducts can lead to undesired reactions of the immune system, which recognizes covalently bonded proteins as foreign. Such immune responses can lead to allergic reactions of varying intensity, called immune toxicity.

The "gold standard" CVB (covalent binding) assay, which detects the formation of covalent adducts by incubation of test compounds with human liver microsomes (HLM) needs to be conducted with 14C-labelled material. This is not appropriate for routine screening purposes. The glutathione assay after metabolic activation (see assay description) is appropriate for routine screening, and compounds that show significant activity in this assay are very likely to show activity in the CVB assay. The above data show that compounds of the invention have a much lower tendency to form covalent drug-glutathion adducts (NO FLAG) while the corresponding reference compounds form significant amounts of glutathione conjugates (FLAG). Generally speaking, compounds of the present invention therefore have a clear advantage with respect to drug safety due to their much less pronounced tendency to form reactive metabolites compared to structurally similar compounds of prior art.

LIST OF EXAMPLES

| Ex. No | Structure | Ec50 [nM] | Efficacy [%] | GSH [HLM] |
| --- | --- | --- | --- | --- |
| Ref. Ex. 20 | 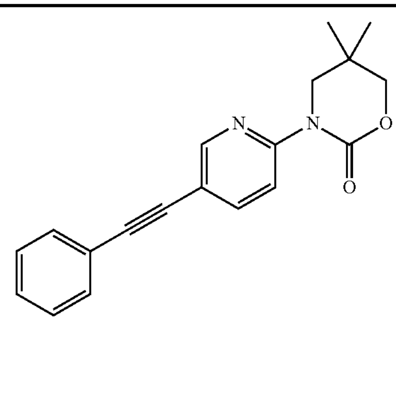 | 27 | 135 | n.m. |

-continued

| Ex. No | Structure | Ec50 [nM] | Efficacy [%] | GSH [HLM] |
|---|---|---|---|---|
| Ref. Ex. 72 | 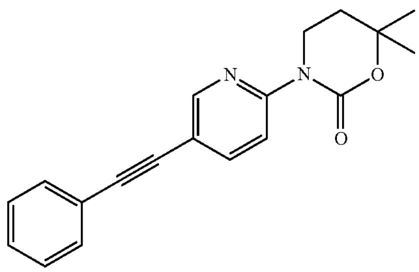 [SMILES: CC1(C)CCN(c2ccc(C#Cc3ccccc3)cn2)C(=O)O1] | 10 | 86 | FLAG |
| Ref. Ex. 76 | 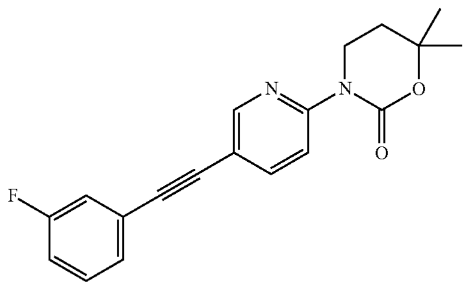 [SMILES: CC1(C)CCN(c2ccc(C#Cc3cccc(F)c3)cn2)C(=O)O1] | 13 | 124 | FLAG |
| Ref. Ex. 79 | 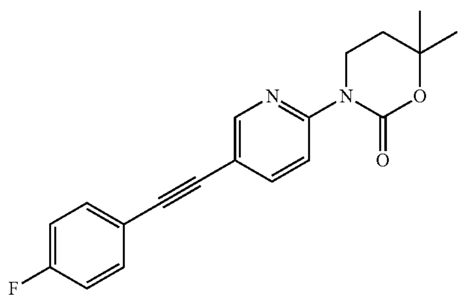 [SMILES: CC1(C)CCN(c2ccc(C#Cc3ccc(F)cc3)cn2)C(=O)O1] | 22 | 85 | FLAG |
| Ref. Ex. 81 | 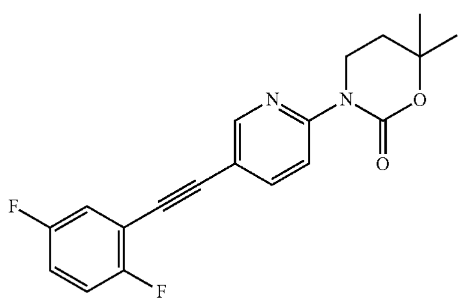 [SMILES: CC1(C)CCN(c2ccc(C#Cc3cc(F)ccc3F)cn2)C(=O)O1] | 12 | 95 | FLAG |
| Ref. Ex. 103 | 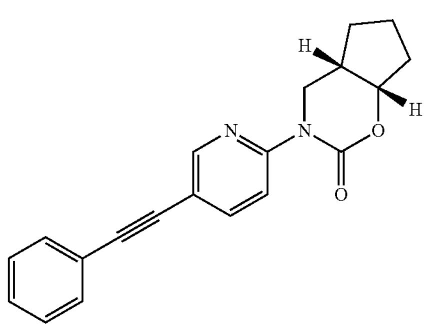 [SMILES: O=C1O[C@H]2CCC[C@H]2CN1c1ccc(C#Cc2ccccc2)cn1] | 27 | 123 | FLAG |

-continued

| Ex. No | Structure | Ec50 [nM] | Efficacy [%] | GSH [HLM] |
|---|---|---|---|---|
| Ex. 1 | (Chiral) | 22 | 38 | NO FLAG |
| Ex. 2 | (Chiral) | 10 | 43 | NO FLAG |
| Ex. 3 | (Chiral) | 10 | 40 | NO FLAG |
| Ex. 4 | (Chiral) | 15 | 35 | NO FLAG |

Compounds of formula I are distinguished by having valuable therapeutic properties. They can be used in the treatment or prevention of disorders, relating to allosteric modulators for the mGluR5 receptor.

The most preferred indications for compounds which are allosteric modulators are schizophrenia and cognition.

The present invention relates to compounds of formula I and to their pharmaceutically acceptable salts, to these compounds as pharmaceutically active substances, to the processes for their production as well as to the use in the treatment or prevention of disorders, relating to allosteric modulators for the mGluR5 receptor, such as schizophrenia and cognition and to pharmaceutical compositions containing the compounds of formula I.

The following definitions of the general terms used in the present description apply irrespective of whether the terms in question appear alone or in combination.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The embodiment of the invention are compounds of formula I

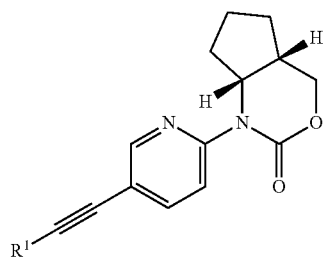

wherein

R¹ is phenyl, 3-fluorophenyl, 4-fluorophenyl or 2,5-di-fluorophenyl;

or a pharmaceutically acceptable acid addition salt, in enantiomerically pure form with the absolute configuration as shown in formula I.

Compounds of formula I are the followings:

(4aS,7aR)-1-(5-Phenylethynyl-pyridin-2-yl)-hexahydro-cyclopenta[d][1,3]oxazin-2-one (4aS,7aR)-1-[5-(3-Fluorophenylethynyl)-pyridin-2-yl]-hexahydro-cyclopenta[d][1,3]oxazin-2-one (4aS,7aR)-1-(5-((4-Fluorophenyl)ethynyl)-pyridin-2-yl)hexahydro-cyclopenta[d][1,3]oxazin-2(1H)-one (4aS,7aR)-1-[5-(2,5-Difluorophenylethynyl)-pyridin-2-yl]-hexahydro-cyclopenta[d][1,3]oxazin-2-one The preparation of compounds of formula I of the present invention may be carried out in sequential or convergent synthetic routes. Syntheses of the compounds of the invention are shown in the following schemes 1 to 3. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula 3

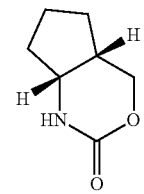

where the compound of formula 3 is a racemic mixture or in enantiomerically pure form with a suitable arylacetylene halo-pyridine compound of formula 4, where Y is halogen, preferably fluorine, bromine or iodine

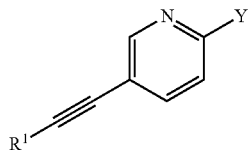

to form a compound of formula I in enantiomerically pure form or as a racemic mixture, where the enantiomers can be separated using methods known to persons skilled in the art,

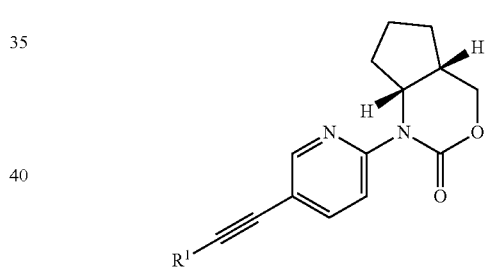

wherein the substituents are described above, or if desired, converting the compounds obtained into pharmaceutically acceptable acid addition salts or by b) reacting a compound of formula II in enantiomerically pure form or as a racemic mixture, where X is halogen, preferably iodine or bromine

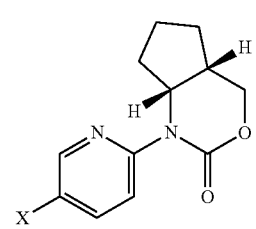

with an acetylene compound of formula 5, where Q is hydrogen or a trialkylsilyl group to form a compound of formula I in enantiomerically pure form or as a racemic mixture which can be separated using methods known to persons skilled in the art, wherein the substituents are described in claim 1, or if desired, converting the compounds obtained into pharmaceutically acceptable acid addition salts.

The preparation of compounds of formula I is further described in more detail in schemes 1 to 3 and in examples 1-4.

The compound of formula 3 can be obtained starting from the racemic or optically pure protected amino-acid of formula 1 by reduction with lithium aluminium hydride in THF to form alcohol 2 which is then cyclized under basic conditions to yield the bicyclic carbamate 3. The halopyridine-arylacetylene 4 is synthesized by Sonogashira coupling of an appropriately substituted arylacetylene derivative 5 (where Q is either hydrogen or an in-situ cleavable protecting group such as a trialkylsilyl- or aryldialkylsilyl-group, preferably hydrogen or trimethylsilyl) with for example 2-fluoro-5-iodopyridine or 2-bromo-5-iodopyridine. Base catalysed nucleophilic substitution (for example NaH/DMF; or $Cs_2CO_3$/Toluene) in the case where Y is fluorine or palladium catalyzed conditions (Buchwald) when Y is bromine in the presence of bicyclic carbamate 3 yield compounds of formula I (scheme 1).

Alternatively, the reaction of carbamate 3 with a dihalopyridine such as 2-fluoro-5 iodopyridine or 2-iodo-5-bromopyridine using conditions described above can also form a compound of formula II where X is iodine or bromine (scheme 2). Compound II is then reacted with an appropriately substituted arylacetylene derivative 5 under Palladium catalyzed coupling conditions (Sonogashira reaction) to form compounds of formula I. Alternatively, the acetylene part can be elaborated in two steps by first reacting compound II with a partially protected acetylene compound such as for example trimethylsilylacetylene to yield an intermediate compound of formula Ib followed by a Sonogashira reaction (in presence of fluoride to cleave the silyl protecting group in-situ) with an appropriately substituted aryl halogenide where X is bromine or iodine to form a compound of formula I. (scheme 3).

Scheme 3

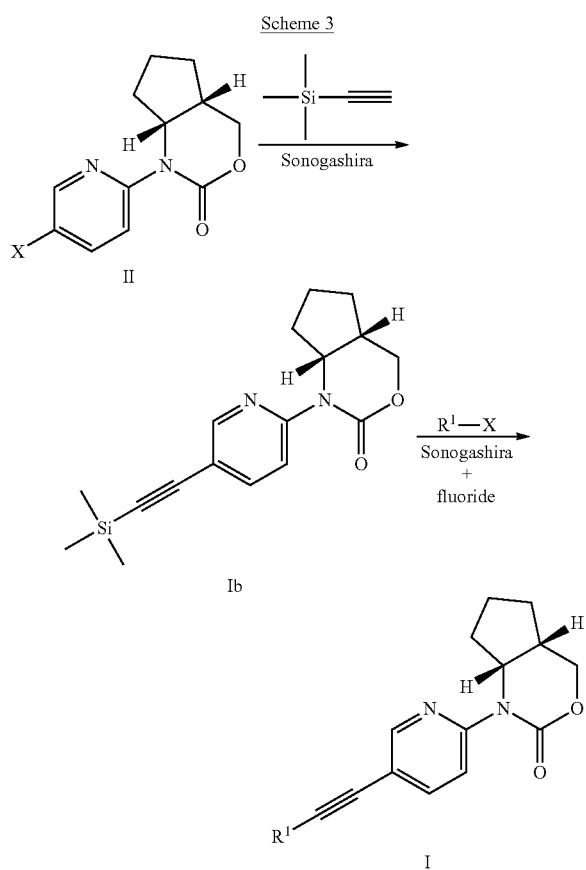

In the case where racemic 3 is used, the enantiomers can be separated at any given stage during the synthesis of compounds of formula I using procedures known to persons skilled in the art.

The compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrome, Down syndrome, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

Biological Assays and Data

The Intracellular $Ca^{2+}$ mobilization assay as described before was used for determination of $EC_{50}$ values.

In the list of examples below are shown the corresponding results for compounds which all have $EC_{50}$ values less or equal 22 nM.

| Example | $EC_{50}$ (nM) mGlu5 PAM |
| --- | --- |
| 1 | 22 |
| 2 | 10 |
| 3 | 10 |
| 4 | 15 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions
Comprising Compounds of the Invention Tablets of the following composition are produced in a conventional manner:

mg/Tablet

| | |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example 1

(4aS,7aR)-1-(5-Phenylethynyl-pyridin-2-yl)-hexahydro-cyclopenta[d][1,3]oxazin-2-one

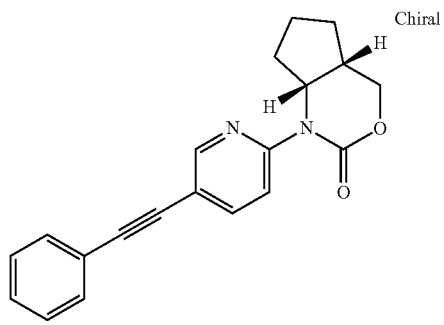 [SMILES: O=C1OC[C@H]2CCC[C@H]2N1c1ccc(C#Cc2ccccc2)cn1]

Step 1:
((1R,2S)-2-Hydroxymethyl-cyclopentyl)-carbamic acid tert-butyl ester

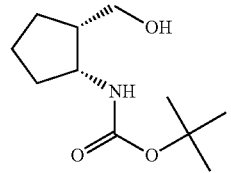

To a well stirred suspension of 0.94 g (24.7 mmol, 2 equiv.) of LiAlH$_4$ in 30 ml of THF at 0° C. was added dropwise at 0° C. a solution of (1S,2R)-methyl 2-(tert-butoxycarbonylamino)-cyclopentanecarboxylate (CAS: 592503-55-4) (3.0 g, 12.3 mmol) (gas evolution, lightly exotherm). After 15 minutes at 0° C. the reaction mixture was allowed to warm up to room temperature and was stirred for 2 h. The mixture was cooled to 0° C. and water was added dropwise. The precipitated inorganic salts were filtered through Celite and were washed with ethyl acetate. The filtrate was evaporated and the residue was purified by column chromatography on silica gel eluting with a 0% to 50% ethyl acetate in heptane gradient to yield 1.99 g (75%) of the title compound as a crystalline white solid which was directly used in the next step.

Step 2:
(4aS,7aR)-Hexahydro-cyclopenta[d][1,3]oxazin-2-one

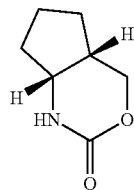

To a solution of ((1R,2S)-2-hydroxymethyl-cyclopentyl)-carbamic acid tert-butyl ester (1.6 g, 7.43 mmol) in THF (40 ml) was added potassium tert-butoxide (3.34 g, 29.7 mmol, 4.0 equiv.) at room temperature. After stirring for 1 h at 60° C. the reaction was allowed to warm up to room temperature and after workup with Ethyl acetate/water, drying and concentration in vacuo, the crude material mixture was adsorbed on silica and chromatographed over a prepacked silica column (50 g, 50% to 100% EtOAc in Heptane gradient) to yield 950 mg (91%) of the title compound as a white solid, which was directly used in the next step.

Step 3: 2-Fluoro-5-phenylethynyl-pyridine

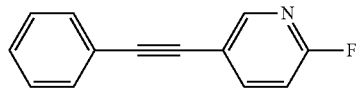

In an 100 ml 2-necked round bottomed flask under Argon were dissolved 2-fluoro-5-iodopyridine (5.0 g, 22.4 mmol, 1.0 equiv.) in THF (30 ml). After 5 minutes at room temperature were added bis(triphenylphosphine)palladium(II)chloride (944 mg, 1.35 mmol, 0.06 equiv.), triethylamine (6.81 g, 9.32 ml, 67.3 mmol, 3.0 equiv.), phenyl acetylene (2.75 g, 2.95 ml, 26.9 mmol, 1.2 equiv.) and copper(I)iodide (128 mg, 0.67 mmol, 0.03 equiv.). The brown suspension was cooled with water (exothermic) to room temperature and stirred overnight. Then 200 ml of diethylether were added, the mixture was filtered, washed with ether and concentrated in vacuum to yield 5.7 g of a brown solid which was adsorbed on silica and was chromatographed in 2 portions over a 100 g prepacked silica column eluting with a 0-10% ethyl acetate in heptane gradient to yield 3.99 g (91%) of the title compound as a light brown solid, MS: m/e=198.1 (M+H⁺).

Step 4: (4aS,7aR)-1-(5-Phenylethynyl-pyridin-2-yl)-hexahydro-cyclopenta[d][1,3]oxazin-2-one In a 10 ml Round bottomed flask were dissolved (4aS, 7aR)-hexahydro-cyclopenta[d]-[1,3]oxazin-2-one (80 mg, 0.57 mmol, 1.0 equiv.) and 2-fluoro-5-(phenylethynyl)pyridine (112 mg, 0.57 mmol, 1.0 equiv.) in 2 ml of DMF. Sodium hydride (60% suspension) (29.5 mg, 0.74 mmol, 1.3 equiv.) were added and the brown suspension was stirred at room temperature overnight. The reaction mixture was quenched with water and extracted twice with ethyl acetate. The combined organic phases were dried, filtered and concentrated. The crude material was purified by flash chromatography over a prepacked silica column eluting with 0-50% ethyl acetate in heptane gradient to yield 42.5 mg of the title compound as colorless amorphous solid, MS: m/e=319.1 (M+H⁺).

Example 2

(4aS,7aR)-1-[5-(3-Fluorophenylethynyl)-pyridin-2-yl]-hexahydro-cyclopenta[d][1,3]oxazin-2-one

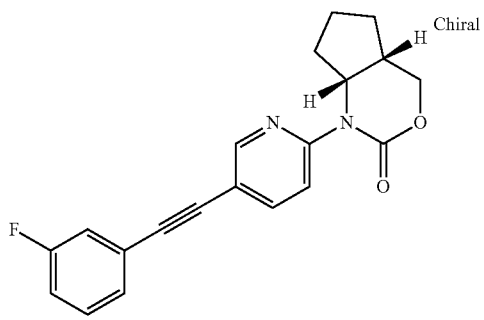 [SMILES: O=C1OC[C@H]2CCC[C@H]2N1c1ccc(C#Cc2cccc(F)c2)cn1]

Step 1: 2-Fluoro-5-(3-fluoro-phenylethynyl)-pyridine

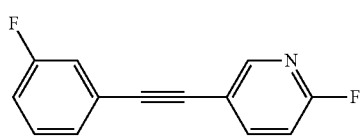 [SMILES: Fc1cccc(C#Cc2ccc(F)nc2)c1]

The title compound was prepared in accordance with the general method of Example 1, step 3 using 3-flurorophenylacetylene instead of phenylacetylene to yield the title compound as a crystalline white solid, MS: m/e=216.2 (M+H⁺).

Step 2: (4aS,7aR)-1-[5-(3-Fluorophenylethynyl)-pyridin-2-yl]-hexahydro-cyclopenta[d][1,3]oxazin-2-one The title compound was prepared in accordance with the general method of Example 1, step 4 using (4aS,7aR)-hexahydro-cyclopenta[d]-[1,3]oxazin-2-one (66 mg, 0.47 mmol) (Example 1, step 2) and 2-fluoro-5-((3-fluorophenyl) ethynyl)pyridine (100 mg, 0.47 mmol) to yield 48 mg (31%) of the title compound as a light yellow amorphous solid; MS: m/e=337.3 (M+H⁺).

Example 3

(4aS,7aR)-1-[5-(4-Fluorophenylethynyl)-pyridin-2-yl]-hexahydro-cyclopenta[d][1,3]oxazin-2-one

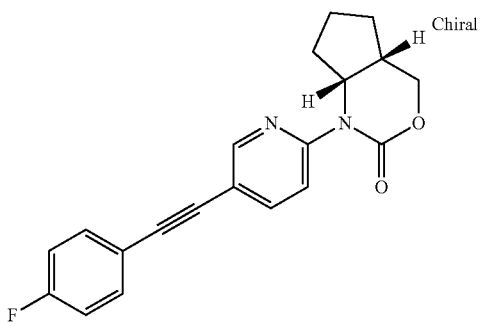 [SMILES: O=C1OC[C@H]2CCC[C@H]2N1c1ccc(C#Cc2ccc(F)cc2)cn1]

Step 1: 2-Fluoro-5-(4-fluoro-phenylethynyl)-pyridine

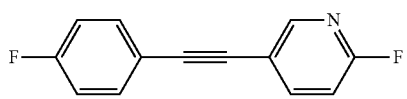 [SMILES: Fc1ccc(C#Cc2ccc(F)nc2)cc1]

The title compound was prepared in accordance with the general method of Example 1, step 3 using 4-flurorophenylacetylene instead of phenylacetylene to yield the title compound as a light brown solid, MS: m/e=216.2 (M+H⁺).

Step 2: (4aS,7aR)-1-[5-(3-Fluorophenylethynyl)-pyridin-2-yl]-hexahydro-cyclopenta[d][1,3]oxazin-2-one The title compound was prepared in accordance with the general method of Example 1, step 4 using (4aS,7aR)-hexahydro-cyclopenta[d][1,3]oxazin-2-one (66 mg, 0.47 mmol) (Example 1, step 2) and 2-fluoro-5-((3-fluorophenyl)

ethynyl)pyridine (100 mg, 0.47 mmol) to yield 22 mg (14%) of the title compound as a colorless oil; MS: m/e=337.4 (M+H+).

Example 4

(4aS,7aR)-1-[5-(2,5-Difluorophenylethynyl)-pyridin-2-yl]-hexahydro-cyclopenta[d]-[1,3]oxazin-2-one

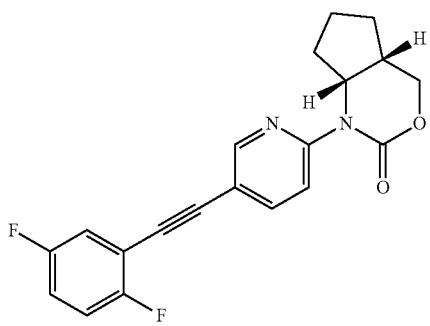 [SMILES: O=C1OC[C@H]2CCC[C@H]2N1c1ccc(C#Cc2cc(F)ccc2F)cn1]

Step 1: (rac)-(4aSR,7aRS)-Hexahydro-cyclopenta[d][1,3]oxazin-2-one

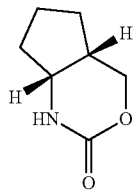

The title compound was prepared in accordance with the same procedures described in example 1, steps 1 and 2, starting from racemic (1SR,2RS)-methyl 2-(tert-butoxycarbonylamino)-cyclopentanecarboxylate (CAS: 164916-42-1) to yield the title compound as a colorless oil; MS: m/e=142.3 (M+H+).

Step 2: 5-(2,5-Difluoro-phenylethynyl)-2-fluoro-pyridine

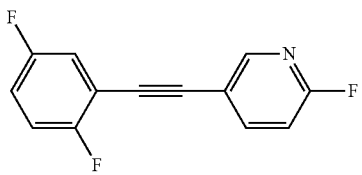 [SMILES: Fc1ccc(F)c(C#Cc2ccc(F)nc2)c1]

The title compound was prepared in accordance with the general method of Example 1, step 3 using 2,5-Difluorophenylacetylene instead of Phenylacetylene to yield the title compound as a yellow solid, MS: m/e=234.4 (M+H+).

Step 3: (rac)-(4aSR,7aRS)-1-[5-(2,5-Difluoro-phenylethynyl)-pyridin-2-yl]-hexahydro-cyclopenta[d][1,3]oxazin-2-one The title compound was prepared in accordance with the general method of Example 1, step 4 using (rac)-(4aSR,7aRS)-hexahydro-cyclopenta[d][1,3]oxazin-2-one (30 mg, 0.21 mmol) (example 4, step 2) and 5-(2,5-difluoro-phenylethynyl)-2-fluoro-pyridine (50 mg, 0.21 mmol) to yield 33 mg (43%) of the title compound as a yellow oil; MS: m/e=355.6 (M+H+).

Step 4: (−)-(4aS,7aR)-1-[5-(2,5-Difluoro-phenylethynyl)-pyridin-2-yl]-hexahydro-cyclopenta[d][1,3]oxazin-2-one A racemic mixture of (rac)-(+/−)-(rac)-(4aSR,7aRS)-1-[5-(2,5-difluoro-phenylethynyl)-pyridin-2-yl]-hexahydro-cyclopenta[d][1,3]oxazin-2-one (Example 1) (33 mg) was separated by chiral HPLC: (Reprosil Chiral NR—5 cm×50 cm, 20 μM; 40% Ethanol/Heptane, 35 ml/min, 18 Bar). One obtains (+)-(4aR,7aS)-1-[5-(2,5-difluoro-phenylethynyl)-pyridin-2-yl]-hexahydro-cyclopenta[d][1,3]oxazin-2-one (15 mg) as a light yellow oil, MS: m/e=355.6 (M+H+) and (−)-(4aR,7aS)-1-[5-(2,5-Difluoro-phenylethynyl)-pyridin-2-yl]-hexahydro-cyclopenta[d][1,3]oxazin-2-one (14.9 mg) as a light yellow oil, MS: m/e=355.6 (M+H+).

The invention claimed is:
1. An ethynyl derivative of formula I

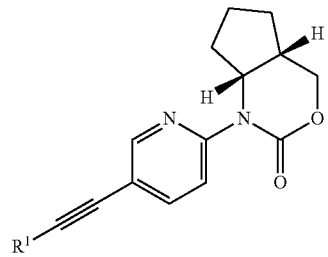

wherein
R$^1$ is phenyl, 3-fluorophenyl, 4-fluorophenyl or 2,5-difluorophenyl;
or a pharmaceutically acceptable acid addition salt in enantiomerically pure form.

2. An ethynyl derivative of formula I, wherein the compound is
(4aS,7aR)-1-(5-Phenylethynyl-pyridin-2-yl)-hexahydro-cyclopenta[d][1,3]oxazin-2-one
(4aS,7aR)-1-[5-(3-Fluorophenylethynyl)-pyridin-2-yl]-hexahydro-cyclopenta[d][1,3]oxazin-2-one
(4aS,7aR)-1-(5-((4-Fluorophenyl)ethynyl)-pyridin-2-yl) hexahydro-cyclopenta[d][1,3]oxazin-2(1H)-one or
(4aS,7aR)-1-[5-(2,5-Difluorophenylethynyl)-pyridin-2-yl]-hexahydro-cyclopenta[d][1,3]oxazin-2-one.

3. A process for preparation of a compound of formula I as described in claim 1, comprising the variants
a) reacting a compound of formula 3

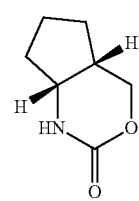

where the compound of formula 3 is a racemic mixture or in enantiomerically pure form with a suitable arylacetylene halo-pyridine compound of formula 4, where Y is halogen, selected from fluorine, bromine or iodine

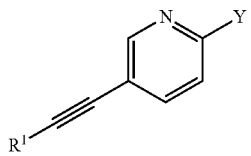

4 to form a compound of formula I in enantiomerically pure form or as a racemic mixture, where the enantiomers can be separated using methods known to persons skilled in the art,

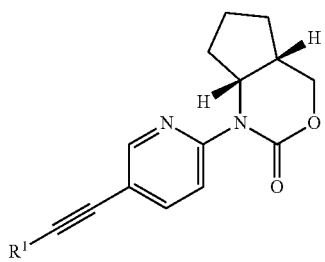

I wherein the substituents are described above, or if desired, converting the compounds obtained into pharmaceutically acceptable acid addition salts or by a) reacting a compound of formula II in enantiomerically pure form or as a racemic mixture, where X is halogen, preferably iodine or bromine

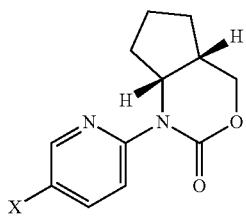

II with an acetylene compound of formula 5, where Q is hydrogen or a trialkylsilyl group

5 to form a compound of formula I in enantiomerically pure form or as a racemic mixture which can be separated using methods known to persons skilled in the art,

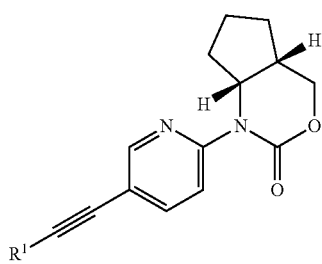

I wherein the substituents are described in claim 1, or if desired, converting the compounds obtained into pharmaceutically acceptable acid addition salts.

4. A pharmaceutical composition comprising at least one compound as defined in formula I according to claim 1 as well as its pharmaceutically acceptable salt.

5. A method for the treatment of schizophrenia, a cognitive disease, fragile X syndrome or autism, which method comprises administering an effective amount of a compound of formula I as described in claim 1 to a patient in need thereof.

* * * * *